US005614627A

United States Patent [19]
Takase et al.

[11] Patent Number: 5,614,627
[45] Date of Patent: Mar. 25, 1997

[54] QUINAZOLINE COMPOUNDS

[75] Inventors: Yasutaka Takase; Nobuhisa Watanabe; Hideyuki Adachi; Kohtaro Kodama; Hiroki Ishihara; Takao Saeki; Shigeru Souda, all of Ibaraki, Japan

[73] Assignee: Eisai Co., Ltd., Japan

[21] Appl. No.: 432,206

[22] PCT Filed: Sep. 12, 1994

[86] PCT No.: PCT/JP94/01504

§ 371 Date: Jun. 27, 1995

§ 102(e) Date: Jun. 27, 1995

[87] PCT Pub. No.: WO95/07267

PCT Pub. Date: Mar. 16, 1995

[30] Foreign Application Priority Data

Sep. 10, 1993 [JP] Japan ..................... 5-248615

[51] Int. Cl.$^6$ .................... C07D 403/04; A61K 31/47
[52] U.S. Cl. ............................................... 544/293
[58] Field of Search ............................. 544/293

[56] References Cited

U.S. PATENT DOCUMENTS

| | | | |
|---|---|---|---|
| 3,470,182 | 9/1969 | Hardtmann et al. | 544/291 |
| 3,560,619 | 2/1971 | Harrison et al. | 544/291 |
| 3,772,295 | 11/1973 | Robba et al. | 260/256.5 |
| 3,814,760 | 6/1974 | Cronin et al. | 544/291 |
| 3,833,584 | 9/1974 | Gabel et al. | 260/256.4 |
| 3,954,987 | 5/1976 | Simpson | 544/291 |
| 3,971,783 | 7/1976 | Barnish et al. | 424/251 |
| 4,098,788 | 7/1978 | Crenshaw et al. | 544/293 |
| 4,188,391 | 2/1980 | Campbell et al. | 424/251 |
| 4,213,987 | 7/1980 | Nakagami et al. | 424/251 |
| 4,309,541 | 1/1982 | Werner | 546/16 |
| 4,323,680 | 4/1982 | Nakagami et al. | 544/291 |
| 4,542,132 | 9/1985 | Campbell et al. | 514/222 |

FOREIGN PATENT DOCUMENTS

| | | |
|---|---|---|
| 317227 | 8/1974 | Austria . |
| 0135318 | 3/1985 | European Pat. Off. . |
| 0326329 | 8/1989 | European Pat. Off. . |
| 0326328 | 8/1989 | European Pat. Off. . |
| 2393531 | 5/1979 | France . |
| 2009472 | 9/1970 | Germany . |
| 2059164 | 6/1971 | Germany . |
| 54-2327 | 9/1979 | Japan . |
| 2-502462 | 7/1990 | Japan . |
| 1182507 | 2/1970 | United Kingdom . |
| 1199768 | 3/1971 | United Kingdom . |
| 1297595 | 11/1972 | United Kingdom . |
| WO9307124 | 4/1993 | WIPO . |

OTHER PUBLICATIONS

Farm. Zh. (Kiev), No. 6, (1979) Grin et al "Structure and antimicrobial activity of N–(4–quinazolyl)–. . .".

J. Med. Chem., vol. 36, No. 24 (1993) Takase et al "Cyclic GMP Phosphodiesterase Inhibitors . . . ".

Chemical Abstracts, vol. 90, No. 28, 1979, Columbus, Ohio, US; abstract No. 87501u, p. 631; *Abstract* & JP–A–78 103 484 (Takeda).

Journal of the American Chemical Society., vol. 70, Jul. 1948, Gaston, PA, US, pp. 2423–2425, A. Tomisek et al. "Quinazolines. VI.Synthesis of 2–Methyl–4–Substituted Quinazolines." *p. 2423–p. 2424*.

*Primary Examiner*—Matthew V. Grumbling
*Attorney, Agent, or Firm*—Nixon & Vanderhye

[57] ABSTRACT

It relates to a quinazoline compound useful as a medicine exhibiting an inhibitory action on calmodulin-dependent cGMP-PDE.

A quinazoline compound represented by the general formula (I) or a pharmacologically acceptable salt thereof:

(wherein $R^1$, $R^2$, $R^3$, $R^4$ and $R^5$ may be the same or different from each other and each represents a hydrogen atom, a lower alkyl group or the like; and $R^6$ and $R^7$ may be the same or different from each other and each represents a hydrogen atom, a carboxyl alkyl group or the like).

3 Claims, No Drawings

QUINAZOLINE COMPOUNDS

This is a national stage application filed under 35 USC 371 of PCT/JP94/01504, filed Sep. 12, 1994.

FIELD OF THE INVENTION

The present invention relates to a quinazoline compound exhibiting an excellent activity as a medicine.

BACKGROUND OF THE INVENTION AND PRIOR ART

Angina pectoris which is one of ischemic heart diseases has been known as a disease which frequently attacks the aged. Although nitrate compounds, nitrite compounds, calcium antagonists, β-blockers and so forth have been used as therapeutic agents for the disease, they are still insufficiently effective in treating angina pectoris or in preventing the evolution thereof into myocardial infarction. Further, lowering in the age of a patient with an ischemic heart disease and complication of the condition thereof have recently occurred owing to, e.g., increasing the stress by change in life style and complication of society. Therefore, a new type of more excellent medicine has been eagerly expected.

Among the above-mentioned medicines which are now in use, those which are each one of medicines which have been used most frequently and which have been used for the longest time are nitrate compounds and nitrite compounds. And it is presumed that cyclic GMP (hereinafter abbreviated to cGMP), which is one of the cyclic nucleotides known as intracellular second messengers, participates in the action of these medicines. The cGMP is well known to have relaxing activities on vascular smooth muscle and bronchial smooth muscle. Although the action mechanism of these medicines is not always apparent, it is generally believed that these medicines activate guanylate cyclase to thereby accelerate the synthesis of cGMP, thus increasing the activity of cGMP. However, these medicines exhibit poor biological availability and a relatively short reaction time. Further, it has been reported that tolerance occurs, which becomes a clinical problem.

Under these circumstances, the present inventors have started searching and studying to develop a new type of more excellent medicine.

Namely, the present inventors have directed their attention to a cGMP phosphodiesterase (hereinafter abbreviated to cGMP-PDE) inhibiting activity and have extensively studied on compounds exhibiting such an activity for a long time. As the result, they have found that a nitrogen-containing condensed heterocyclic compound which will be described below exhibits such an activity and hence is efficacious against various ischemic heart diseases and the like. Thus, the present invention has been accomplished.

Although literatures disclosing quinazoline derivatives useful as medicines include, e.g., Toku-hyo Hei. 2-502462 and WO9307124, the compounds disclosed therein are different from the compound of the present invention in both structure and function.

DISCLOSURE OF THE INVENTION

The present invention relates to a quinazoline compound represented by the general formula (I) or a pharmacologically acceptable salt thereof:

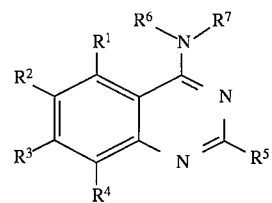

(wherein $R^1$, $R^2$, $R^3$, $R^4$ and $R^5$ may be the same or different from each other and each represents a hydrogen atom, a halogen atom, a lower alkyl group or a lower alkoxy group; and $R^6$ and $R^7$ may be the same or different from each other and each represents a hydrogen atom, a lower alkyl group, a hydroxyalkyl group, a lower alkoxyalkyl group, a cyanoalkyl group, a heteroarylalkyl group, a cycloalkyl group, a cycloalkylalkyl group or a carboxyl alkyl group which may be protected, or alternatively $R^6$ and $R^7$ may form a ring together with the nitrogen atom to which they are bonded, this ring optionally having a substituent).

In the general formula (I), the lower alkyl group in the definitions of $R^1$, $R^2$, $R^3$, $R^4$, $R^5$, $R^6$ and $R^7$ means a linear or branched alkyl group having 1 to 6 carbon atoms, for examples, methyl, ethyl, n-propyl, n-butyl, isopropyl, isobutyl, 1-methylpropyl, tert-butyl, n-pentyl, 1-ethylpropyl, isoamyl and n-hexyl. The most desirable examples include methyl group and ethyl group.

The lower alkoxy group in the definitions of $R^1$, $R^2$, $R^3$, $R^4$ and $R^5$ means methoxy group, ethoxy group, propoxy group, butoxy group and the like which are derived from the above lower alkyl groups. Preferable ones include methoxy group and ethoxy group, and particularly preferable one includes methoxy group.

The hydroxyalkyl group in the definitions of $R^6$ and $R^7$ means the one wherein one or, two or more hydroxyl group(s) is(are) bonded to any of the carbon atoms of the lower alkyl group described above.

The lower alkoxyalkyl group in the definitions of $R^6$ and $R^7$ means the one wherein one or, two or more lower alkoxy group(s) defined above is(are) bonded to any of the carbon atoms of the alkyl group described above.

The cyanoalkyl group in the definitions of $R^6$ and $R^7$ means the one wherein one or, two or more cyano group(s) is(are) bonded to any of the carbon atoms of the lower alkyl group described above.

The heteroarylalkyl group in the definitions of $R^6$ and $R^7$ means the one wherein one or, two or more heteroaryl group(s) is(are) bonded to any of the carbon atoms of the lower alkyl group described above. The heteroaryl group means a five- to six-membered ring containing one to three nitrogen atom, sulfur atom and/or oxygen atom, and preferable ones include aromatic rings containing one or two nitrogen atoms, such as imidazolyl group, pyridyl group and pyrimidyl group.

The cycloalkyl group in the definitions of $R^6$ and $R^7$ means the one having 3 to 8 carbon atoms, and preferably ones include those having 5 to 6 carbon atoms.

The cycloalkylalkyl group in the definitions of $R^6$ and $R^7$ means the one wherein the cycloalkyl group defined above is bonded to any of the carbon atoms of the lower alkyl group described above.

The alkyl group constituting the carboxyl alkyl group which may be protected in the definitions of $R^6$ and $R^7$ has the same meaning as that of the lower alkyl group described above. The carboxyl group in this case may be bonded to any of the carbon atoms of the alkyl group. The protective group for the carboxyl group includes lower alkyl groups such as methyl, ethyl and t-butyl; phenyl-substituted lower alkyl groups wherein the phenyl group may have a substituent, such as p-methoxybenzyl, p-nitrobenzyl, 3,4-dimethoxybenzyl, diphenylmethyl, tributyl and phenethyl; halogenated lower alkyl groups such as 2,2,2-trichloroethyl and 2-iodoethyl; lower alkanoyloxy lower alkyl groups such as pivaloyloxymethyl, acetoxymethyl, propionyloxymethyl, butyryloxymethyl, valeryloxymethyl, 1-acetoxyethyl, 2-acetoxyethyl, 1-pivaloyloxyethyl and 2-pivaloyloxyethyl; higher alkanoyloxy lower alkyl groups such as palmitoyloxyethyl, heptadecanoyloxymethyl and 1-palmitoyloxyethyl; lower alkoxycarbonyloxy lower alkyl groups such as methoxycarbonyloxymethyl, 1-butoxycarbonyloxyethyl and 1-(isopropoxycarbonyloxy)ethyl; carboxy lower alkyl groups such as carboxymethyl and 2-carboxyethyl; a heterocyclic group such as 3-phthalidyl; benzoyloxy lower alkyl groups which may have a substituent, such as 4-glycyloxybenzoyloxymethyl and 4-[N-(t-butoxycarbonyl)glycyloxy]benzoyloxymethyl; a (substituted dioxolene) lower alkyl group such as (5-methyl-2-oxo1,3-dioxolen-4-yl)methyl; a cycloalkyl-substituted lower alkanoyloxy lower alkyl group such as 1-cyclohexylacetyloxyethyl; and a cycloalkyloxycarbonyloxy lower alkyl group such as 1-cyclohexyloxycarbonyloxyethyl.

Further, they may form various acid amides. They may be any one as far as it is a protective group which can release a carboxyl group by the decomposition thereof in vivo. The quinazoline compound of the present invention exhibits its drug efficacy either by decomposing the protective group in vivo or as such.

The ring which is formed from the $R^6$ and $R^7$ together with the nitrogen atom to which they are bonded in the "$R^6$ and $R^7$ may form a ring together with the nitrogen atom to which they are bonded, this ring optionally forming a substituent" means a five- to six-membered saturated ring. This ring may further contain a nitrogen atom, an oxygen atom or a sulfur atom in addition to the nitrogen atom to which $R^6$ and $R^7$ are bonded.

The substituent in this case means, e.g., a lower alkyl group, a carboxyl group which may be protected, a cyano group, an acyl group, an amino group which may have a substituent, an aryl group which may have a substituent, a heteroaryl group which may have a substituent, an arylalkyl group which may have a substituent, a heteroarylalkyl group which may have a substituent or the group represented by formula =O. Preferable substituents include carboxyl groups which may be protected, and still more preferable one includes a carboxyl group.

The halogen atom in the definitions of $R^1$, $R^2$, $R^3$, $R^4$ and $R^5$ means fluorine atom, chlorine atom, bromine atom and iodine atom.

The pharmacologically acceptable salt according to the present invention includes inorganic acid salts such as hydrochloride, sulfate, hydrobromide and phosphate; and organic acid salts such as formate, acetate, trifluoroacetate, maleate, fumarate, tartrate, methanesulfonate, benzenesulfonate and toluenesulfonate.

Some of the compounds may form hydrates, which also fall within the scope of the present invention, of course.

Desirable examples of the compound of the present invention include quinazoline compounds represented by the following general formula (I') and pharmacologically acceptable salts thereof:

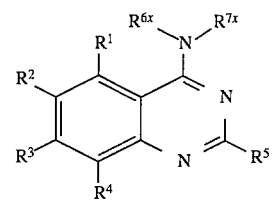

(wherein $R^1$, $R^2$, $R^3$, $R^4$ and $R^5$ may be the same or different from each other and each represents a hydrogen atom, a halogen atom, a lower alkyl group or a lower alkoxy group; and $R^{6x}$ and $R^{7x}$ may be the same or different from each other and each represents a hydrogen atom, a lower alkyl group or a carboxyl alkyl group which may be protected, or alternatively $R^{6x}$ and $R^{7x}$ may form a ring together with the notrogen atom to which they are bonded, this ring optionally having a substituent).

Among them, preferables are those wherein $R^{6x}$ and $R^{7x}$ may be the same or different from each other and each represents a hydrogen atom or a carboxyl alkyl group which may be protected, or those wherein $R^6$ and $R^7$ form a ring which may have a substituent, together with the nitrogen atom to which they are bonded.

More desirable compounds among the preferable compounds described above include quinazoline compounds represented by the following general formula (Ia) or pharmacologically acceptable salts thereof:

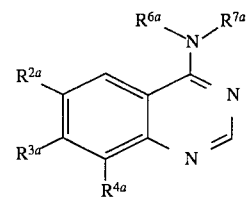

(wherein $R^{2a}$, $R^{3a}$ and $R^{4a}$ may be the same or different from each other and each represents a halogen atom or a lower alkoxy group; and $R^{6a}$ and $R^{7a}$ may be the same or different from each other and each represents a hydrogen atom, a lower alkyl group or a carboxyl alkyl group which may be protected, or alternatively $R^{6a}$ and $R^{7a}$ may form a ring together with the nitrogen atom to which they are bonded, this ring optionally having a substituent).

Further, the most desirable compounds among the compounds of the present invention include quinazoline compounds represented by the following general formula (Ib) or pharmacologically acceptable salts thereof:

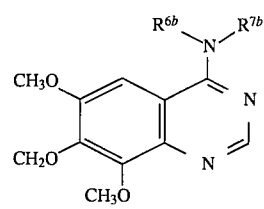

(wherein $R^{6b}$ and $R^{7b}$ may be the same or different from each other and each represents a hydrogen atom, a n-propyl group or a carboxypropyl group which may be protected, or alternatively $R^{6b}$ and $R^{7b}$ may form a six-membered ring together with the nitrogen atom to which they are bonded, this ring optionally having a substituent).

Compounds wherein $R^{6b}$ and $R^{7b}$ form a piperidine ring together with the nitrogen atom to which they are bonded are preferable, and compounds wherein this piperidine ring has a carboxyl group which may be protected at the 4-position thereof are the most preferable. Main processes for the preparation of the compound of the present invention will now be described.

Preparation process 1

The compound represented by the general formula (I) can be prepared by the following process.

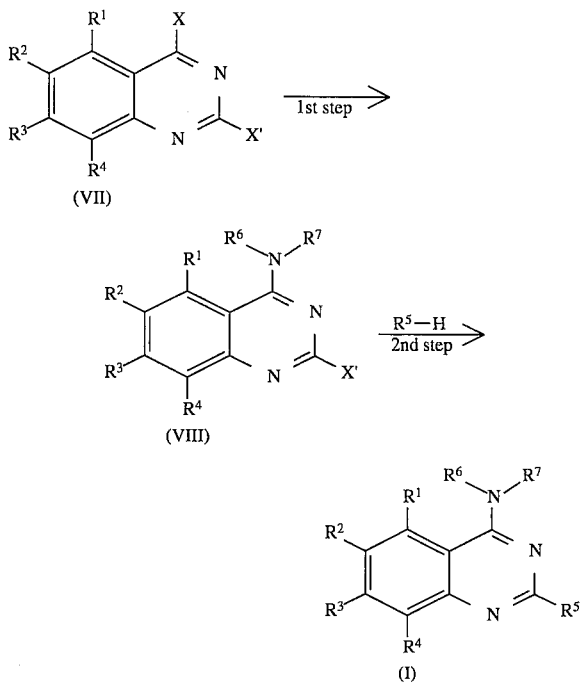

(wherein $R^1$, $R^2$, $R^3$, $R^4$, $R^5$, $R^6$ and $R^7$ each has the meaning described above; and X and X' may be the same or different from each other and each means a halogen atom).

(1st step)

That is, it is a condensation reaction according to a conventional process.

Although it is preferable to use an alcoholic solvent such as isopropyl alcohol, an etheric solvent such as tetrahydrofuran, or dimethylformamide as the reaction solvent, any organic solvent inert to the reaction can be used.

When the reaction is made to proceed in the presence of a tertiary amine such as triethylamine under reflux by heating with the removal of formed hydrochloric acid, still preferable results can be attained.

(2nd step)

It is a reaction which comprises condensing the compound (VIII) obtained in the 1st step with a compound represented by the general formula $R^5$-H by a conventional process.

Although it is preferable to use an alcoholic solvent such as isopropyl alcohol, an etheric solvent such as tetrahydrofuran, or dimethylformamide as the reaction solvent, any organic solvent inert to the reaction can be used.

In this step, it is preferable that the reaction is conducted under reflux by heating in the presence of an organic base such as triethylamine, pyridine and ethyldiisopropylamine; an inorganic base such as sodium carbonate, potassium carbonate, sodium hydrogencarbonate, sodium hydride and sodium hydroxide; an alkoxide such as sodium methoxide and potassium t-butoxide; or the like.

Preparation process 2

When $R^1$, $R^3$ or $R^4$ in the general formula (I) is a hydrogen atom, they can be prepared also by the following process.

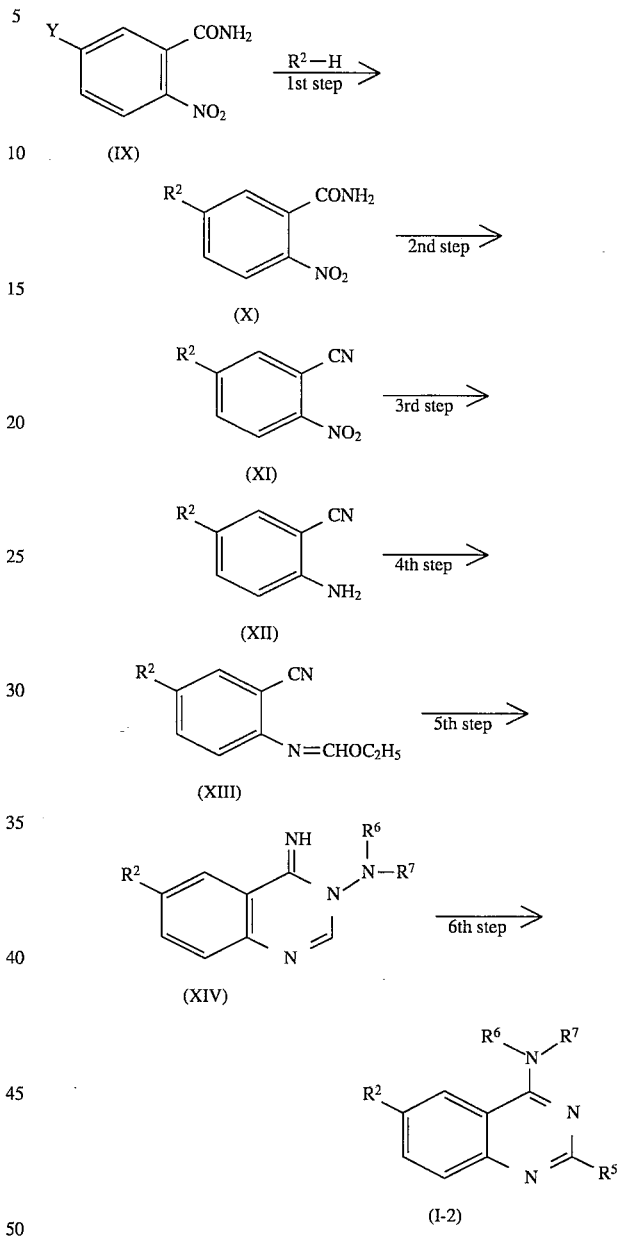

(wherein $R^2$, $R^5$, $R^6$ and $R^7$ each has the meaning described above; and Y means a halogen atom).

(1st step)

That is, it is a reaction which comprises obtaining a compound (X) by treating a halogenated benzamide derivative with a compound corresponding to the desired compound in a solvent in the presence of a base at a temperature ranging from room temperature to the boiling point of the solvent.

Tetrahydrofuran, N,N-dimethylformamide, N-methylpyrrolidone or the like is preferably used as the solvent, though any one, which is inert to this reaction, may be used.

Preferable examples of the base include potassium carbonate, hydrides of alkali metals and alkaline earth metals such as lithium hydride and calcium hydride; alkoxides such as potassium t-butoxide and sodium ethoxide; sodium amide and the like.

(2nd step)

It is a reaction which comprises obtaining a compound (XI) by dehydrating the benzamide derivative obtained in the 1st step.

Although the reaction is generally conducted under heating, the reaction proceeds sufficiently even at room temperature. Preferable examples of the dehydrating reagent include trifluoroacetic anhydride, thionyl chloride, chlorosulfonyl isocyanate, p-toluenesulfonyl chloride, phosphorus pentachloride, phosphorus oxychloride and the like.

Preferable examples of the reaction solvent include etheric solvents such as tetrahydrofuran and dioxane, acetonitrile, N,N-dimethylformamide, triethylamine, pyridine and the like, though any one, which is inert to the reaction, can be used.

(3rd step)

That is, it is a step which comprises obtaining an aniline derivative represented by the general formula (XII) by reducing the nitrobenzene derivative obtained in the 2nd step.

It is preferable that the reaction is conducted in a polar solvent, for example, water or an alcoholic solvent such as methanol and ethanol.

The reaction is generally made to proceed under the acidic condition with acetic acid or hydrochloric acid by the addition of a metal such as iron, tin or zinc.

The reaction temperature ranges from room temperature to the refluxing temperature of the solvent.

(4th step)

That is, it is a process which comprises obtaining a compound represented by the general formula (XIII) by heating in ethyl orthoformate in the presence of an acid such as trifluoroacetic acid, p-toluenesulfonic acid and concentrated hydrochloric acid.

(5th step)

That is, it is a reaction which comprises condensing the compound (XIII) obtained in the 4th step with an amine corresponding to the desired compound through ring closure by a conventional process.

As the reaction solvent, alcoholic ones such as methanol and ethanol can be used. The reaction temperature is preferably around 50° C., though it may range from room temperature to the boiling point of the solvent.

(6th step)

It is a reaction which comprises obtaining an objective compound (I-2) by heating the compound (XIV) obtained in the 5th step in a solvent.

The preferable reaction solvents include alcoholic solvents such as methanol and ethanol, though any solvent inert to the reaction can be used.

Further, more desirable results can be obtained when the reaction is conducted in the presence of an alkali such as aqueous sodium hydroxide and potassium carbonate.

The compounds obtained by the above processes can be converted into salts by a conventional process such as the addition of sodium hydroxide, potassium hydroxide, methanesulfonyl chloride or the like.

Preparation process A

Among the starting compounds (VII) to be used in the preparation of the compound represented by the general formula (I), the compound (VII') wherein $R^1$, $R^3$ and $R^4$ are hydrogen atoms can be prepared by the following process.

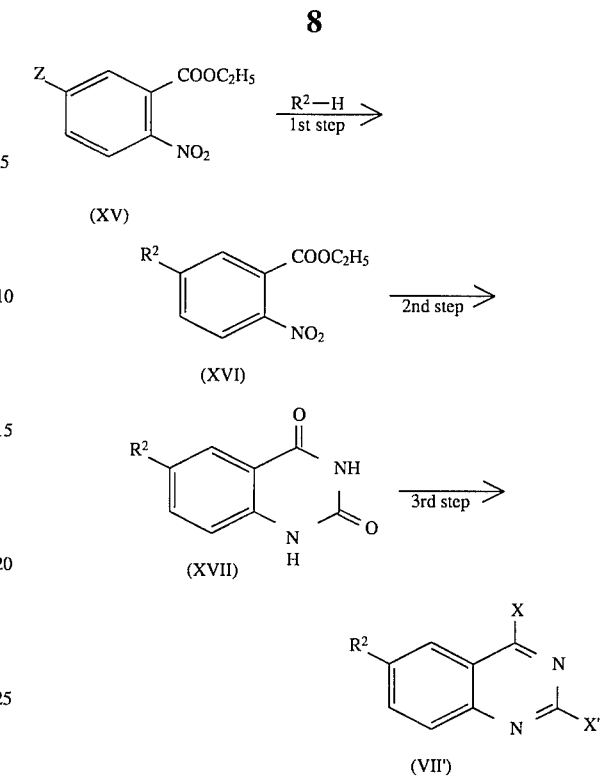

(in a series of the formulas. $R^2$, X and X' each has the meaning described above; and Z means a halogen atom).

(1st step)

That is, it is a reaction which comprises obtaining a compound (XVI) by treating a benzene derivative with a compound corresponding to the desired compound in a solvent in the presence of a base at a temperature ranging from room temperature to the boiling point of the solvent.

Tetrahydrofuran, N,N-dimethylformamide, N-methylpyrrolidone and the like are preferably used as the solvent, though any solvent inert to the reaction can be used.

Preferable examples of the base include potassium carbonate; hydrides of alkali metals and alkaline earth metals such as lithium hydride and calcium hydride; alkoxides such as potassium t-butoxide and sodium ethoxide; sodium amide and the like.

(2nd step)

That is, it is a step which comprises obtaining a compound (XVII) from the compound (XVI) through ring closure by a conventional process. For example, a process which comprises reacting a urea derivative with the compound (XVI) to effect ring closure, and the like may be cited.

The reaction temperature in this case is preferably about 170° to 190° C., and preferable examples of the reaction solvent include N-methylpyrrolidone and the like, though any organic solvent inert to the reaction can be used.

(3rd step)

That is, it is a halogenation reaction. This step can be conducted by a conventional process, and, for example, a process which comprises refluxing in the presence of phosphorus pentachloride and phosphorus oxychloride or in the presence of phosphorus oxychloride by heating under stirring to effect chlorination, and the like can be cited.

Pharmacological Experimental Example will now be described to illustrate the usefulness of the compound of the present invention in detail.

Pharmacological Experimental Example
Study on enzyme-inhibitory activity with calmodulin-dependent cGMP-phosphodiesterase obtained from swine aorta 1. Experimental method The enzyme activity of calmodulin-dependent cGMP-phosphodiesterase (hereinafter referred to CaM-PDE) prepared from swine aorta was determined according to the method of Thompson et al. The emzyme activity was determined in the presence of 1 mM of calcium ion ($Ca^{++}$) and calmodulin (250 U/ml) by the use of 1 μM of cGMP as the substrate. The compound of the present invention was dissolved in DMSO and added to the reaction liquid. The final concentration of DMSO in the reaction solution was adjusted to 4% or below.

The preparation of the CaM-PDE was effected according to the method [Saeki, T. and Saito, I., Isolation of cyclic nucleotide phosphodiesterase isozymes from pig aorta, Biochem. Pharmacol. in press] by the use of swine aorta.

2. Experimental results

The CaM-PDE inhibitory activity of the compounds of the present invention as determined by the above method are given in Table 1.

TABLE 1

| Ex. No. | $IC_{50}$ |
|---|---|
| 2 | 0.48 |
| 3 | 2.35 |
| 7 | 4.62 |
| 10 | 53.9 |
| 12 | 3.50 |
| 13 | 2.37 |
| 14 | 1.29 |
| 15 | 3.62 |
| 16 | 1.65 |
| 18 | 0.73 |
| 20 | 0.42 |
| 32 | 6.40 |
| 35 | 1.90 |
| 38 | 7.90 |
| 40 | 0.17 |
| 41 | 0.30 |
| 43 | 0.74 |
| 51 | 4.30 |
| 57 | 11.6 |
| 58 | 2.80 |
| 61 | 1.10 |
| 62 | 0.74 |
| 65 | 10.7 |
| 68 | 4.00 |

It is clarified from the Experimental Example described above that the compound of the present invention exhibits an inhibitory activity on PDE, particularly CaM-PDE. Namely, it is clarified that the compound of the present invention exhibits the effect of increasing the in vivo concentration of cGMP because it exhibits an inhibitory activity on CaM-PDE. Accordingly, the quinazoline compound, which is the compound of the present invention, is effective in preventing and treating diseases against which a CaM-PDE inhibitory action is efficacious. Examples of such diseases include ischemic heart diseases such as angina pectoris, myocardial infarction, and chronic and acute cardiac failure; pulmonary hypertension accompanied or not accompanied by cor pulmonale; hypertension caused by various factors; peripheral circulatory disturbance; brain circulatory disturbance; cerebral malfunction; allergic diseases such as bronchial asthma, atopic dermatitis and allergic rhinitis; and the like.

Further, the compound of the present invention is lowly toxic and highly safe, thus the present invention is valuable also in this sence.

When the present invention is used as a medicine for such diseases, it is administered by oral administration or parenteral administration. The dose thereof varies depending upon the extent of symptom; the age, sex, weight and drug sensitivity of a patient; the method, timing and interval of administration; the type of pharmaceutical preparation; the type of a medicine to be administered together therewith; the type of an active ingredient and so forth, and is not particularly limited.

In the oral administration, generally about 0.1 to 1000 mg, still more preferably 1 to 500 mg, per adult a day, is administered in 1 to 3 portions a day.

In the injection, the daily dose is generally about 1 μg/kg to 3000 μg/kg, preferably about 3 μg/kg to 1000 μg/kg.

When a solid preparation for oral administration is prepared, a process which comprises adding a filler and, if necessary, a binder, a disintegrator, a lubricant, a color, a corrigent and the like to the basis and then shaping it into a tablet, a coated tablet, a granule, a powder, a capsule or the like, may be cited.

Examples of the filler to be used include lactose, corn starch, sucrose, glucose, sorbitol, crystalline cellulose and silicon dioxide; those of the binder to be used include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin; those of the lubricant to be used include magnesium stearate, talc, polyethylene glycol, silica and hardened vegetable oil; those of the color to be used include those authorized as pharmaceutical additives; and those of the corrigent to be used include cocoa powder, menthol, aromatic powder, mentha oil, borneol and powdered cinnamon bark. Of course, the tablet and granule may be those having sugar coating or gelatin coating, or those which are suitably coated at need.

When an injection is prepared, a pH regulator, a buffer, a suspending agent, a solubilizing agent, a stabilizer, an isotonizing agent, a preservative and the like are added to the basis at need, followed by forming into an injection for intravenous, subcutaneous or intramuscular administration by a conventional process. If necessary, a freeze-dried product is prepared by a conventional process.

Examples of the suspending agent include methylcellulose, Polysorbate 80, hydroxyethylcellulose, acacia, tragacanth powder, sodium carboxymethylcellulose, polyoxyethylene sorbitan monolaurate and the like.

Examples of the solubilizing agent include polyoxyethylene hardened castor oil Polysorbate 80, nictoinamide, polyoxyethylene sorbitan monolaurate, macrogol, ethyl ester of castor oil fatty acid and the like.

EXAMPLE

Examples will now be described to facilitate the understanding of the present invention. It is needless to say that the present invention is not limited to them.

Example 1

4-(3-Ethoxycarbonylpropyl)amino-6,7,8-trimethoxyquinazoline

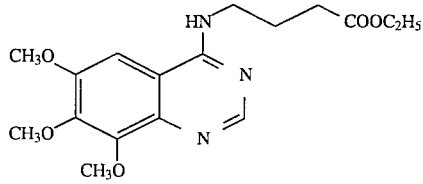

1.0 g of ethyl 4-aminobutyrate hydrochloride (6.0 mmol), 2 ml of triethylamine, 10 ml of tetrahydrofuran and 10 ml of 2-propanol were added to 0.50 g (2.0 mmol) of 4-chloro-6,7,8-trimethoxyquinazoline, followed by heating under reflux one whole day and night. The reaction liquid was distilled under reduced pressure to remove the solvent. The obtained residue was purified by silica gel column chromatography (ethyl acetate) and then recrystallized from ethyl acetate/hexane. Thus, 0.49 g (yield 72%) of a white crystal was obtained.

Mol. form. $C_{17}H_{23}N_3O_5$
Yield 72%
M.p. 123° to 124° C.
Mass 350 ($M^+$+1)
NMR δ ($CDCl_3$); 1.25(3H, t, J=7.2 Hz) 2.10(2H, quintet, J=6.4 Hz) 2.57(2H, t, J=6.4 Hz) 3.68(2H, m) 4.00(3H, s) 4.03(3H, s) 4.11(3H, s) 4.14(2H, q, J=7.2 Hz) 6.56(1H, br-s) 6.86(1H, s) 8.60(1H, s)

Example 2

4-(3-Carboxypropyl)amino-6,7,8-trimethoxyquinazoline

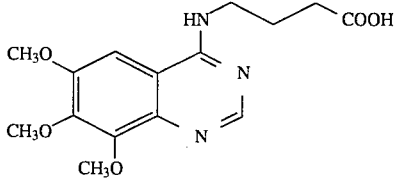

5 ml of a 1N aqueous solution of sodium hydroxide was added to a solution of 0.52 g (1.5 mmol) of the 4-(3-ethoxycarbonylpropyl)amino-6,7,8-trimethoxyquinazoline obtained in Example 1 in tetrahydrofuran (5 ml)/ethanol (5 ml), followed by stirring at room temperature one whole day and night. The reaction liquid was neutralized with 5 ml of 1N hydrochloric acid, and then concentrated under reduced pressure. The crystals thus precipitated were recovered by filtration, washed with water, and dried with air. Thus, 0.36 g (yield 744%) of a pale-yellow crystal was obtained.

Mol. form. $C_{15}H_{19}N_3O_5$
Yield 74%
M.p. 236° to 237° C. (dec.)
NMR δ (DMSO-$d_6$); 1.88(2H, quintet, J=7.2 Hz) 2.33(2H, t, J=7.2 Hz) 3.55(2H, m) 3.87(3H, s) 3.91(3H, s) 3.97(3H, s) 7.44(1H, s) 8.04(1H, brt, J=5.4 Hz) 8.35(1H, s)

The following compounds were obtained in accordance with the processes of Examples 1 and 2.

Example 3

4-(5-Ethoxycarbonylpentyl)amino-6,7,8-trimethoxyquinazoline

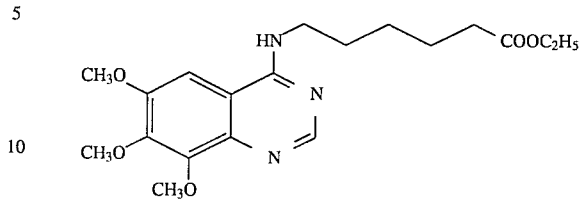

Mol. form. $C_{19}H_{27}N_3O_5$
Yield 84%
M.p. 128° to 129° C.
Mass 378($M^+$+1)
NMR δ ($CDCl_3$); 1.25(3H, t, J=7.2 Hz) 1.49(2H, m) 1.67–1.80(4H, m) 2.35(2H, t, J=7.0 Hz) 3.68(2H, dt, J=6.8, 6.0 Hz) 3.99(3H, s) 4.03(3H, s) 4.11(3H, s) 4.12(2H, q, J=7.2 Hz) 5.72(1, brs) 6.80(1H, s) 8.61(1H, s)

Example 4

4-(5-Ethoxycarbonylpentyl)amino-6-chloroquinazoline

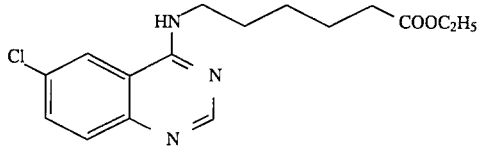

Mol. form. $C_{16}H_{20}ClN_3O_2$
Yield 84%
M.p. 117° to 118° C.
Mass 322($M^+$+1)
NMR δ ($CDCl_3$); 1.27(3H, t, J=7.2 Hz) 1.49(2H, m) 1.68–1.80(4H, m) 2.37(2H, t, J=7.0 Hz) 3.71(2H, dt, J=6.8, 5.6 Hz) 4.18(2H, q, J=7.2 Hz) 6.03(1H, br-s) 7.66(1H, dd, J=9.2, 2.4 Hz) 7.77(1H, d, J=9.2 Hz) 7.82(1, d, J=2.4 Hz) 8.64(1H, s)

Example 5

4-(Ethoxycarbonylmethyl)amino-6,7,8-trimethoxyquinazoline

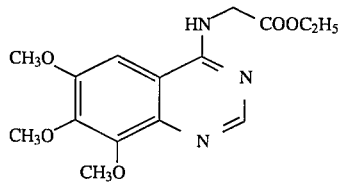

Mol. form. $C_{15}H_{19}N_3O_5$
Yield 84%
M.p. 182° to 183° C. (dec.)
Mass 322($M^+$+1)
NMR δ ($CDCl_3$); 1.35(3H, t, J=7.2 Hz) 3.94(3H, s) 4.04(3H, m) 4.11(3H, s) 4.31(2H, q, J=7.2 Hz) 4.40(2H,d, J=4.8 Hz) 6.23(1H, brt. J=4.8 Hz) 6.76(1H, s) 8.61(1H, s)

EXAMPLE 6

4-(6-Ethoxycarbonylhexyl)amino-6,7,8-trimethoxyquinazoline

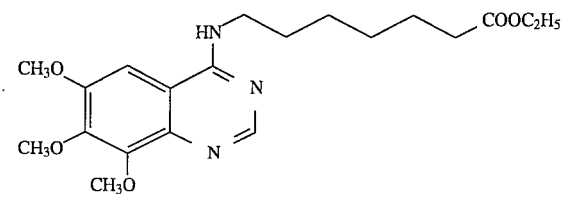

Mol. form. $C_{20}H_{29}N_3O_5$
Yield 98%
M.p. 132° to 133° C.
Mass 392($M^+$+1)
NMR δ (CDCl$_3$); 1.25(3H, t, J=7.2 Hz) 1.36–1.51(4H, m) 1.60–1.79(4H, m) 2.31(2H, t, J=7.2 Hz) 3.65(2H, dt, J=7.2, 5.6 Hz) 3.98(3H, s) 4.03(3H, s) 4.12(3H, s) 4.13(2H, q, J=7.2 Hz) 5.54(1H, brs) 6.72(1H, s) 8.62(1H, s)

Example 7

4-(2-Ethoxycarbonylethyl)amino-6,7,8-trimethoxyquinazoline

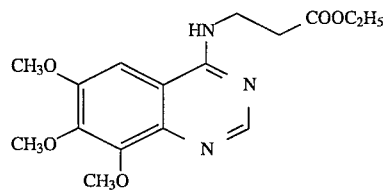

Mol. form. $C_{16}H_{21}N_3O_5$
Yield 57%
M.p. 141° to 142° C.
Mass 336 ($M^+$+1)
NMR δ (CDCl$_3$); 1.28(3H, t, J=7.2 Hz) 2.76(2H, t, J=6.0 Hz) 3.95(2H, q, J=6.0 Hz) 3.98(3H, s) 4.03(3H, s) 4.12(3H, s) 4.18(2H, q, J=7.2 Hz) 6.23(1H, brs) 6.69(1H, s) 8.61(1H, s)

Example 8

4-(4-Ethoxycarbonylbutyl)amino-6,7,8-trimethoxyquinazoline

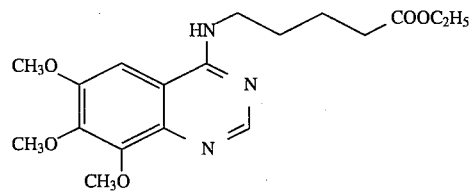

Mol. form. $C_{18}H_{25}N_3O_5$
Yield 35%
M.p. 139° to 140° C.
Mass 364 ($M^+$+1)
NMR δ (CDCl$_3$); 1.28(3H, t, J=7.2 Hz) 1.74–1.86(4H, m) 2.44(2H, t, J=6.6 Hz) 3.64(2H, m) 4.00(3H, s) 4.03(3H, s) 4.12(3H, s) 4.16(2H, q, J=7.2 Hz) 6.10(1H, brs) 6.92(1H, s) 8.61(1H, s)

Example 9

4-(7-Ethoxycarbonylheptyl)amino-6,7,8-trimethoxyquinazoline

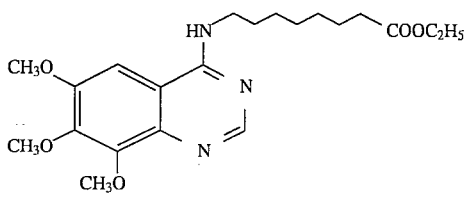

Mol. form. $C_{21}H_{31}N_3O_5$
Yield 61%
M.p. 124° to 125° C.
Mass 406($M^+$+1)
NMR δ (CDCl$_3$); 1.25(3H, t, J=7.0 Hz) 1.30–1.48(6H, m) 1.63(2H, m) 1.73(2H, m) 2.30(2H, t, J=7.4 Hz) 3.64(2H, dt, J=7.2, 5.6 Hz) 3.98(3H, s) 4.03(3H, s) 4.12(3H, s) 4.12(2H, q, J=7.0 Hz) 5.53(1H, brs) 6.72(1H, s) 8.62(1H, s)

Example 10

4-(5-Carboxypentyl)amino-6-chloroquinazolne

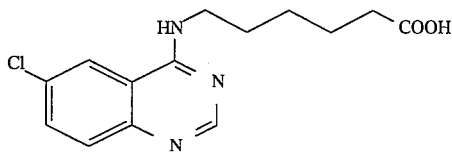

Mol. form. $C_{14}H_{16}ClN_3O_2$
Yield quantitative
M.p. 215° to 216° C.
NMR δ (CDCl$_3$); 1.37(2H, m) 1.57(2H, quintet, J=7.4 Hz) 1.65(2H, quintet, J=7.4 Hz) 2.22(2H, t, J=7.2 Hz) 3.52(2H, dt, J=7.2, 5.2 Hz) 7.68(1H, d, J=8.8 Hz) 7.75(1H, dd, J=8.8, 2.4 Hz) 8.32(1H, brt, J=5.2 Hz) 8.40(1H, d, J=2.4 Hz) 8.46(1H, s) 11.98(1H, br-s)

Example 11

4-(Carboxymethyl)amino-6,7,8-trimethoxyquinazoline

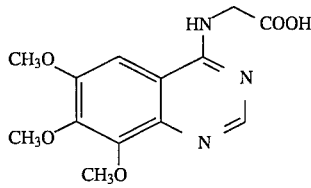

Mol. form. $C_{13}H_{15}N_3O_5$
Yield 54%
M.p. 121° to 123° C.
NMR δ (DMSO-d$_6$); 3.89(3H, s) 3.92(3H, s) 3.99(3H, s) 4.18(2H, d, J=5.6 Hz) 7.49(1H, s) 8.37(1H, s) 8.47(1H, brt, J=5.6 Hz)

Example 12

4-(6-Carboxyhexyl)amino-6,7,8-trimethoxyquinazoline

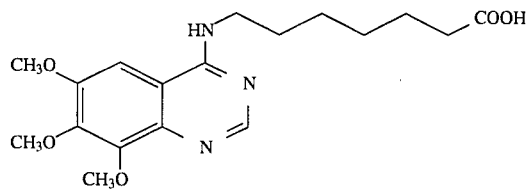

Mol. form. $C_{18}H_{25}N_3O_5$
Yield 894%
M.p. 184° to 185° C.
NMR δ (DMSO-$d_6$); 1.28–1.42 (4H, m) 1.52(2H, m) 1.64(2H, m) 2.20(2H, t, J=7.2 Hz) 3.51(2H, m) 3.87(3H, s) 3.91(3H, s) 3.97(3H, s) 7.43(1H, s) 7.99(1H, brt, J=5.6 Hz) 8.35(1H, s)

Example 13

4-(2-Carboxyethyl)amino-6,7,8-trimethoxyquinazoline

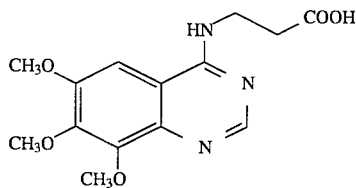

Mol. form. $C_{14}H_{17}N_3O_5$
Yield 56%
M.p. 236° to 237° C. (dec.)
NMR δ (DMSO-$d_6$); 2.65(2H, t, J=7.0 Hz) 3.37(2H, dt, J=7.0, 5.6 Hz) 3.88(3H, s) 3.91(3H, s) 3.98(3H, s) 7.43(1H, s) 8.11(1H, brt, J=5.6 Hz) 8.38(1H, s)

Example 14

4-(4-Carboxybutyl)amino-6,7,8-trimethoxyuinazoline

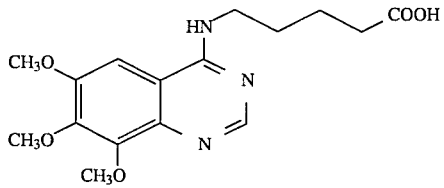

Mol. form. $C_{16}H_{21}N_3O_5$
Yield 34%
M.p. 208° to 209° C. (dec.)
NMR 67 (DMSO-$d_6$); 1.54–1.72(4H, m) 2.28(2H, t, J=7.0 Hz) 3.54(2H, m) 3.87(3H, s) 3.91(3H, s) 3.97(3H, s) 7.44(1H, s) 8.04(1H, brt, J=5.6 Hz) 8.35(1H, s) 12.01(1H, brs)

Example 15

4-(7-Carboxyheptyl)amino-6,7,8,-trimethoxyquinazoline

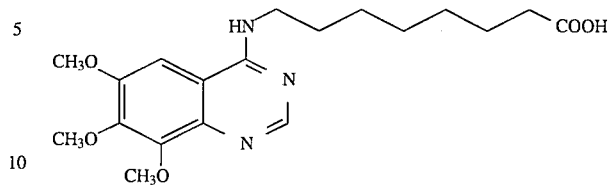

Mol. form. $C_{19}H_{27}N_3O_5$
Yield 74%
M.p. 180° to 181° (dec.)
NMR δ (DMSO-$d_6$); 1.24–1.41(6H, m) 1.51(2H, m) 1.64(2H, m) 2.19(2H, t, J=7.4 Hz) 3.52(2H, m) 3.87(3H, s) 3.91(3H, s) 3.97(3H, s) 7.44(1H, s) 7.99(1H, brt, J=5.6 Hz) 8.35(1H, s) 11.94(1H, brs)

Example 16

4-(5-Carboxypentyl)amino-6,7,8-trimethoxyquinazoline

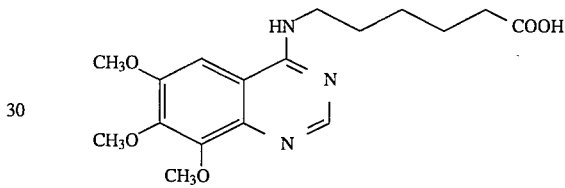

Mol. form. $C_{17}H_{23}N_3O_5$
Yield 76%
M.p. 213° to 214° C. (dec.)
NMR δ (DMSO-$d_6$); 1.38(2H, m) 1.57(2H, m) 1.65(2H, m) 2.23(2H, t J=7.2 Hz) 3.52(2H, dt, J=7.2, 5.6 Hz) 3.88(3H, s) 3.91(3H, s) 3.97(3H, s) 7.44(1H, s) 8.04(1H, brt, J=5.6 Hz) 8.35(1H, s) 11.99 (1H, brs)

Example 17

4-[N-(3-Ethoxycarbonylpropl)-N-methylamino]-6,7,8-trimethoxyquinazoline hydrochloride

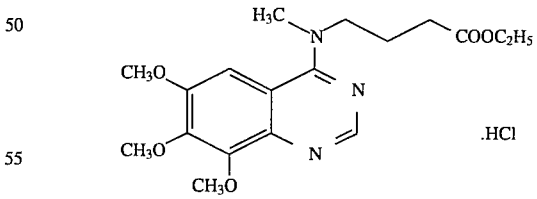

Mol. form. $C_{18}H_{25}N_3O_5$ · HCl
Yield 67%
M.p. 94° to 96° C. (dec.)
NMR δ (DMSO-$d_6$); 1.15(3H, t, J=7.2 Hz) 2.01(2H, m) 2.41(2H, t, J=7.2 Hz) 3.64(3H, br-s) 3.95(2H) 3.96(3H, s) 3.97(3H, s) 3.99(3H, s) 4.03(2H, q, J=7.2 Hz) 7.45(1H, s) 8.57(1H, s)

Example 18

4-[N-(3-Carboxypropyl)-N-methylaminol-]6,7,8,-trimethoxyquinazoline

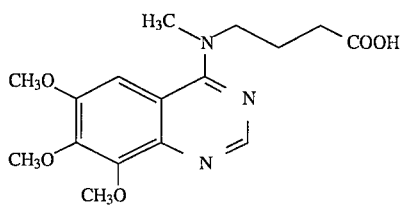

Mol. form. $C_{16}H_{21}N_3O_5$
Yield 87%
NMR δ (DMSO-$d_6$); 1.97 (2H, quintet, J=7.2 Hz) 2.27 (2H, t, J=7.2 Hz) 3.22(3H, s) 3.61(2H, t, J=7.2 Hz) 3.89(3H, s) 3.90(3H, s) 3.96(3H, s) 7.10(1H, s) 8.41(1H, s)

Example 19

4-(4-Ethoxycarbonylpiperidino)-6,7,8-trimethoxyquinazoline

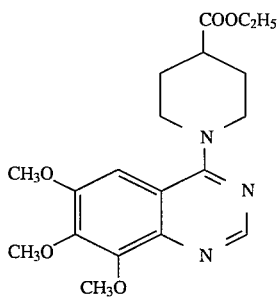

Mol. form. $C_{19}H_{25}N_3O_5$
Yield 88%
M.p. oily substance
NMR δ (DMSO-$d_6$); 1.30 (3H, t, J=7.0 Hz) 1.98(2H, m) 2.12(2H, m) 2.63(1H, m) 3.14(2H, m) 3.97(3H, s) 4.06(3H, 4.10(2H, m) 4.13(3H, s) 4.19(2H, q, J=7.0 Hz) 6.92(1H, s) 8.73(1H, s)

Example 20

4-(4-Carboxypiperidino)-6,7,8-trimethoxyquinazoline

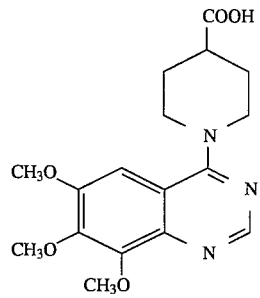

Mol. form. $C_{17}H_{21}N_3O_5$
Yield 77%
M.p. 233° to 234° C. (dec.)
Mass 348($M^+$+1)
NMR δ (DMSO-$d_6$); 1.80(2H, m) 1.99(2H, m) 2.59(1H, m) 3.18(2H, m) 3.92(3H, s) 3.93(3H, s) 4.01(3H, s) 4.09(2H, m) 6.69(1H, s) 8.55(1H, s) 12.29(1H, br-s)

Example 21

4-(6-Ethoxycarbonylhexyl)amino-6,7,8-trimetboxyquinazoline

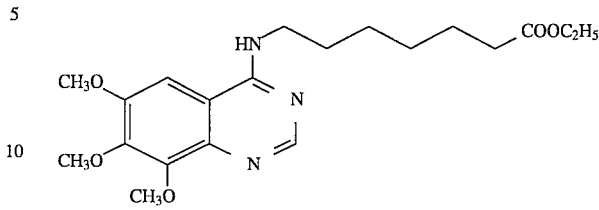

Mol. form. $C_{20}H_{29}N_3O_5$
Yield 98%
M.p. 132° to 133° C.
Mass 392° ($M^+$+1)
NMR δ (CDCl$_3$); 1.25(3H, t, J=7.2 Hz) 1.36–1.51(4H, m) 1.60–1.79(4H, m) 2.31(2H, t, J=7.2 Hz) 3.65(2H, dt, J=7.2, 5.6 Hz) 3.98(3H, s) 4.03(3H, s) 4.12(3H, s) 4.13(2H, q, J=7.2 Hz) 5.54(1H, brs) 6.72(1H, s) 8.62(1H, s)

Example 22

4-(5-Ethoxycarbonylpentyl)amino-6-chloroquinazoline

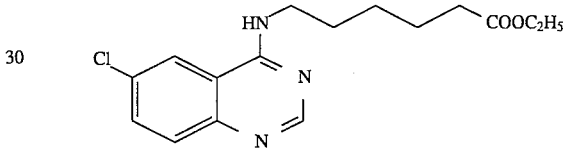

Mol. form. $C_{16}H_{20}ClN_3O_2$
Yield 84%
M.p. 117° to 118° C.
Mass 322 ($M^+$+1)
NMR δ (CDCl$_3$); 1.27(3H, t, J=7.2 Hz) 1.49(2H, m) 1.68–1.80(4H, m) 2.37(2H, t, J=7.0 Hz) 3.71(2H, dt, J=6.8, 5.6 Hz) 4.18(2H, q, J=7.2 Hz) 6.03(1H, brs) 7.66(1H, dd, J=9.2, 2.4 Hz) 7.77(1H, d, J=9.2 Hz) 7.82(1H, d, J=2.4 Hz) 8.64(11, s)

Example 23

4-[N-(3-Ethoxycarbonylpropyl-N-methylamino)-6,7,8-trimethoxyquinazoline hydrochloride

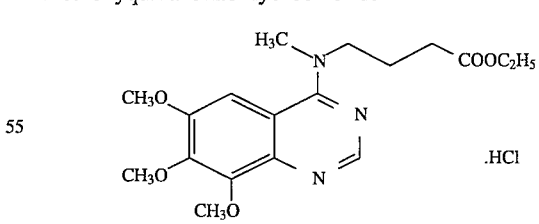

Mol. form. $C_{18}H_{25}N_3O_5$·HCl
Yield 67%
M.p. 94° to 96° C.
NMR δ (DMSO-$d_6$); 1.15(3H, t, J=7.2 Hz) 2.01(2H, m) 2.41(2H, t, J=7.2 Hz) 3.64(3H, brs) 3.95(2H) 3.96(3H, s) 3.97(3H, s) 3.99(3H, s) 4.03(2H, q, J=7.2 Hz) 7.45(1H, s) 8.57(1H, s)

Example 24

4-(3-Ethoxycarbonylpropyl)amino-6,8-dimethoxyquinzoline

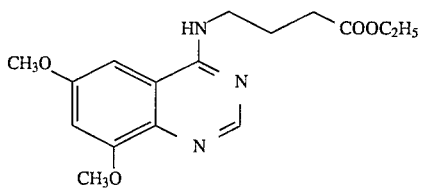

Mol. form. $C_{16}H_{21}N_3O_4$
Yield 90%
M.p. 133° to 134° C.
Mass 320($M^+$+1)
NMR δ (CDCl$_3$); 1.25(3H, t, J=7.2 Hz) 2.10(2H, quintet, J=6.4 Hz) 2.55(2H, t, J=6.4 Hz) 3.69(2H, dt, J=6.4, 4.8 Hz) 3.93(3H, s) 4.00(3H, s) 4.14(2H, q, J=7.2 Hz) 6.49(1H, brs) 6.61(1H, d, J=2.4 Hz) 6.75(1H, d, J=2.4 Hz) 8.59(1H, s)

Example 25

4-(3-Ethoxycarbonylpropyl)amino-8-methoxyquinazoline

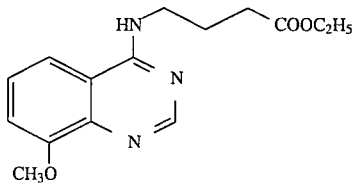

Mol. form. $C_{15}H_{19}N_3O_3$
Yield 64%
M.p. 128° to 129° C.
Mass 290($M^+$+1)
NMR δ (CDCl$_3$); 1.24 (3H, t, J=7.2 Hz) 2.09 (2H, quintet, J=6.4 Hz) 2.53(2H, t, J=6.4 Hz) 4.04(3H, s) 4.15(2H, q, J=7.2 Hz) 6.44(1H, brs) 7.11 (1H, dd, J=8.0, 0.8 Hz) 7.30(1H, dd, J=8.0, 0.8 Hz) 7.4(1H, t, J=8.0 Hz) 8.69(1H, s)

Example 26

4-(3-Ethoxycarbonylpropyliamino-6-chloroquinazoline

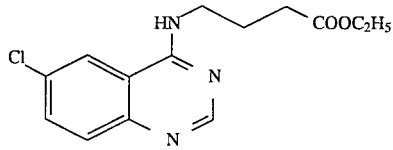

Mol. form. $C_{14}H_{16}ClN_3O_2$
Yield 57%
M.p. 91° to 92° C.
Mass 294($M^+$+1)
NMR δ (CDCl$_3$); 1.26(3H, t, J=7.2 Hz) 2.10(2H, quintet, J=6.4 Hz) 2.54(2H, t, J=6.4 Hz) 3.70(2H, dt, J=6.4, 5.2 Hz) 4.18(2H, q, J=7.2 Hz) 6.60(1H, brs) 7.66(1H, dd, J=9.2, 2.0 Hz) 7.76(1H, d, J=2.0 Hz) 7.77(1H, d,, J=9.2 Hz) 8.63(1H, s)

Example 27

4-(3-Ethoxycarbonylpropyl)amino-7-chloroquinazoline

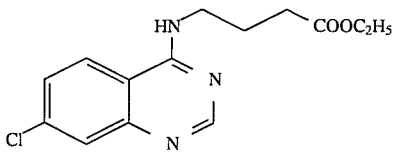

Mol. form. $C_{14}H_{16}ClN_3O_2$
Yield 36%
M.p. 90° to 91° C.
Mass 294($M^+$+1)
NMR δ (CDCl$_3$); 1.25(3H, t, J=7.2 Hz) 2.09(2H, quintet, J=6.4 Hz) 2.55(2H, t, J=6.4 Hz) 3.70(2H, dt, J=6.4, 4.8 Hz) 4.16(2H, q, J=7.2 Hz) 6.74(1H, brs) 7.42(1H, dd, J=8.8, 2.0 Hz) 7.71(1H, d, J=8.8 Hz) 7.81(1H, d, J=2.0 Hz) 8.62(1H, s)

Example 28

4-(Carboxymethyl)amino-6,7,8-trimethoxyquinazoline

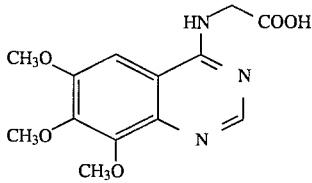

Mol. form. $C_{13}H_{15}N_3O_5$
Yield 54%
M.p. 121° to 123° C.
Mass 294($M^+$+1)
NMR δ (DMSO-d$_6$); 3.89(3H, s) 3.92(3H, s) 3.99(3H, s) 4.18(2H, d, J=5.6 Hz) 7.49(1H, s) 8.37(1H, s) 8.47(1H, brt, J=5.6 Hz)

Example 29

4-(6-Carboxyhexyl)amino-6,7,8-trimethoxyquinazoline

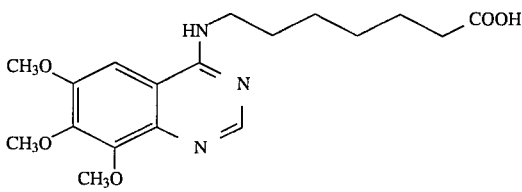

Mol. form. $C_{18}H_{25}N_3O_5$
Yield 89%
M.p. 184° to 185° C.
Mass 364 ($M^+$+1)
NMR δ (DMSO$_6$); 1.28–1.42(4H, m) 1.52(2H, m) 1.64(2H, m) 2.20(2H, t, J=7.2 Hz) 3.51(2H, m) 3.87(3H, s) 3.91(3H, s) 3.97(3H, s) 7.43(1H, s) 7.99(1H, brt, J=5.6 Hz) 8.35(1H, s)

Example 30

4-[N-(3-Carboxypropyl)-N-methylamino]-6,7,8-trimethoxyquinazoline

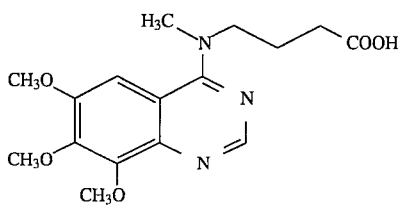

Mol. form. $C_{16}H_{21}N_3O_5$
Yield 87%
M.p. 133° to 135° C.
NMR δ (DMSO$_6$); 1.97(2H, quintet, J=7.2 Hz) 2.27 (2H, t, J=7.2 Hz) 3.22 (3H, s) 3.61(2H, t, J=7.2 Hz) 3.89(3H, s) 3.90(3H, s) 3.96(3H, s) 7.10(1H, s) 8.41(1H, s)

Example 31

4-(3-Carboxypropyl)amino-6,8-dimethoxyquinazoline

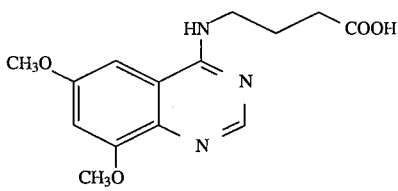

Mol. form. $C_{14}H_{17}N_3O_4$
Yield 51%
M.p. 217° to 218° C. (dec.)
NMR δ (DMSO$_6$); 1.89(2H, quintet, J=7.2 Hz) 2.33 (2H, t, J=7.2 Hz) 3.55(2H, dt, J=7.2, 5.6 Hz) 3.88(3H, s) 3.89(3H, s) 6.83(1H, d, J=2.4 Hz) 7.17(1H, d, J=2.4 Hz) 7.99(1H, brt, J=5.6 Hz) 8.31(1H, s)

Example 32

4-(4-Cyanobutyl)amino-6,7,8-trimethoxyquinzaoline

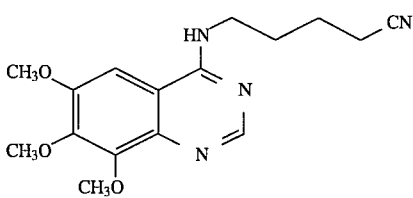

Mol. form. $C_{16}H_{20}N_4O_3$
Yield 94%
M.p. 160° to 161° C.
Mass 317 (M$^+$+1)
NMR δ (DMSO-d$_6$); 1.81(2H, m) 1.94(2H, m) 2.47(2H, t, J=6.8 Hz) 3.75(2H, dt, J=6.8, 6.0 Hz) 4.00(3H, s) 4.03(3H, s) 4.11(3H, s) 5.91(1H, brs) 6.82(1H, s) 8.60(1H, s)

Example 33

4-(5-Cyanopentyl)amino-6,7,8-trimethoxyquinazoline

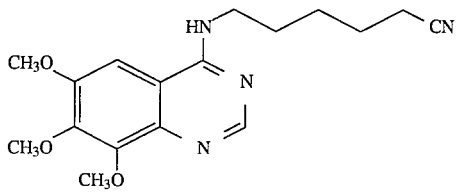

Mol. form. $C_{17}H_{22}N_4O_3$
Yield 75%
M.p. 155° to 156° C.
Mass 331 (M$^+$+1)
NMR δ (DMSO-D$_6$); 1.60–1.80(6H, m) 2.40(2H, t, J=7.0 Hz) 3.70(2H, dt, J=7.0, 5.6 Hz) 4.00 (3H, s) 4.03(3H, s) 4.11(3H, s) 6.00 (1H, brs) 6.84(1H, s) 8.60(1H, s)

Example 34

4-(2-Hydroxyethyl)amino-6,7,8-trimetboxyquinazoline

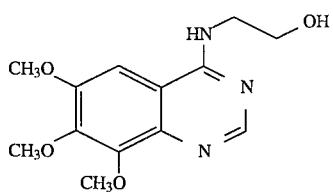

Mol. form. $C_{13}H_{17}N_3O_4$
Yield 80%
M.p. 183° to 185° C.
Mass 280 (M$^+$+1)
NMR δ (CDCl$_3$); 3.78(2H, m) 3.88(2H, m) 3.99(3H, s) 4.03(3H, s) 4.10(3H, s) 7.10(1H, brs) 7.13(1H, s) 8.53(1H, s)

Example 35

4-(3-Hydroxypropyl)amino-6,7,8-trimethoxyquinazoline

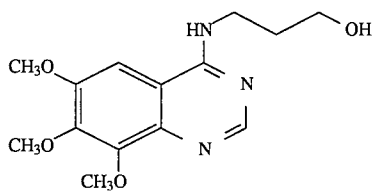

Mol. form. $C_{14}H_{19}N_3O_4$
Yield 76%
M.p. 179° to 180° C.
Mass 294 (M$^+$+1)
NMR δ (CDCl$_3$); 1.89(2H, m) 3.70(2H, t, J=5.4 Hz) 3.85(2H, q, J=6.0 Hz) 3.97(3H, s) 4.03(3H, s) 4.11(3H, s) 6.07(1H, brs) 6.72(1H, s) 8.56(1H, s)

Example 36

4-(4-Hydroxybutyl)amino-6,7,8-trimethoxyquinazoline

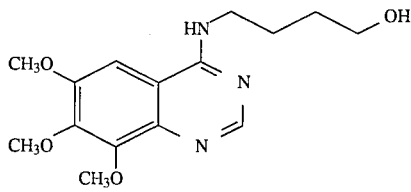

Mol. form. $C_{15}H_{21}N_3O_4$
Yield 74%
M.p. 171° to 182° C.
Mass 308 (M$^+$+1)
NMR δ (CDCl$_3$); 1.74(2H, m) 1.88(2H, quintet, J=6.8 Hz) 3.69(2H, dt, J=6.8, 5.6 Hz) 3.80 (2H, t, J=6.0 Hz) 3.96 (3H, s) 4.03(3H, s) 4.11(3H, s) 6.17(1H, brs) 6.77(1H, s) 8.59(1H, s)

Example 37

[3-(Imidazol-1-yl)propyl]amino-6,7,8-trimethoxyquinazoline

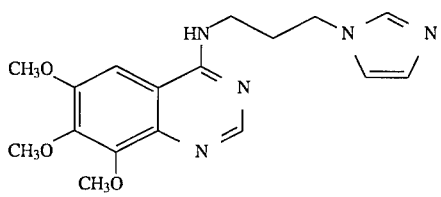

Mol. form. $C_{17}H_{21}N_5O_3$
Yield 82%
M.p. 192° to 194° C.
Mass 344 (M$^+$+1)
NMR δ (DMSO-d$_6$); 2.13(2H, quintet, J=7.0 Hz) 3.53(2H, m) 3.88(3H, s) 3.92(3H, s) 3.97(3H, s) 4.13(2H, t, J=7.0 Hz) 7.07(1H, s) 7.35(1H, s) 7.47(1H, s) 8.00(1H, s) 8.20(1H, t, J=5.4 Hz) 8.38(1H, s)

Example 38

6-Chloro-4-[3-(imidazol-1-yl)propyl]aminoquinazoline

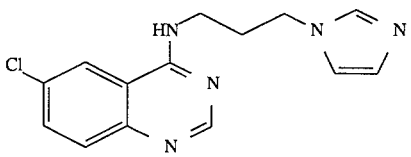

Mol. form. $C_{14}H_{14}ClN_5$
Yield 63%
M.p. 165° to 168° C.
Mass 288 (M$^+$+1)

NMR δ (CDCl$_3$); 2.24(2H, quintet, J=6.4 Hz) 3.64(2H, q, J=6.4 Hz) J=6.4 Hz) 7.08(1H, s) 7.09(1H, s) 4.14(2H, t, 7.64(1H, dd, J=8.8, 2.4 Hz) 7.73(1H, d, J=8.8 Hz) 7.92(1H, s) 8.06(1H, brs) 8.38(1H, d, J=2.4 Hz) 8.58(1H, s)

Example 39

4-Dipropylamino-6,7,8-trimethoxyquinazoline hydrochloride

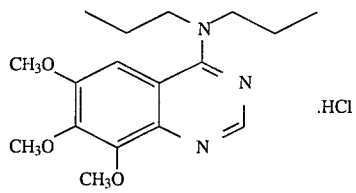

Mol. form. $C_{17}H_{25}N_3O_3HCl$
Yield 78%
M.p. 169° to 170° C.
NMR δ (CDCl$_3$);
1.08(6H, t, J=7.2 Hz) 1.92(4H, brm) 3.80(4H, m) 3.97(3H, s) 4.09(3H, s) 4.19(3H, s) 7.02(1H, s) 8.78(1H, s)

Example 40

4-Propylamino-6,7-trimethoxyquinazoline

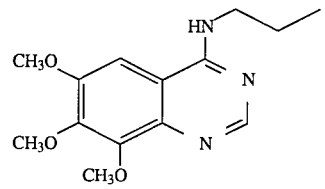

Mol. form. $C_{14}H_{19}N_3O_3$
Yield 87%
NMR δ (CDCl$_3$); 1.05(3H, t, J=7.2 Hz) 1.77 (2H, sextet, J=7.2 Hz) 3.62(2H, dt, J=7.2, 6.0 Hz) 3.98(3H, s) 4.03(3H, s) 4.12(3H, s) 5.50(1H, brs) 6.69(1H, s) 8.63(1H, s)

Example 41

4-Diethylamino-6,7,8-trimethoxyquinazoline hydrochloride

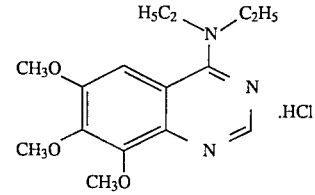

Mol. form. $C_{15}H_{21}N_3O_3 \cdot HCl$
Yield quantitative
M.p. 122° to 123° C.
Mass 292 (M$^+$+1)

NMR δ (CDCl₃); 1.51(6H, t, J=6.8 Hz) 3.93(4H, q, J=6.8 Hz) 3.98(3H, s) 4.10(3H, s) 4.20(3H, s) 7.08(1H, s) 8.80(1H, s)

Example 42

4-Diethylamino-6,7-dimethoxyquinazaline hydrochloride

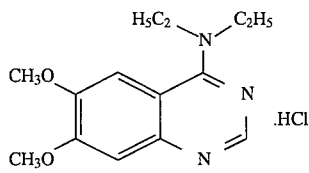

Mol. form. C₁₄H₁₉N₃O₂.HCl
Yield 87%
M.p. 218° to 219° C.
NMR δ (CDCl₃); 1.51(6H, t, J=7.2 Hz) 3.91(4H, q, J=7.2 Hz) 3.99(3H, s) 4.10(3H, s) 7.25(1H, s) 7.93(1H, s) 8.47(1H, d, J=2.8 Hz)

Example 43

4-Diethylamino-6,8-dimethoxyquinazoline hydrochloride

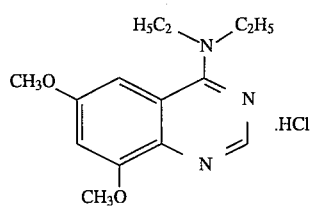

Mol. form. C₁₄H₁₉N₃O₂.HCl
Yield quantitative
M.p. 160° to 161° C.
NMR δ (CDCl₃); 1.51(6H, brt) 3.91(3H, s) 3.94(4H, q, J=7.2 Hz) 4.10 (3H, s) 6.85(1H, d, J=2.4 Hz) 6.91(1H, d, J=2.4 Hz) 8.82(1H, s)

Example 44

4-Diethylaminoquinazoline hydrochloride

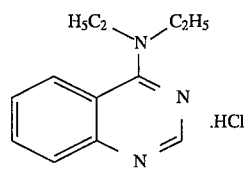

Mol. form. C₁₂H₁₅N₃.HCl
Yield 96%
M.p. 207° to 208° C.
NMR δ (CDCl₃); 1.52(6H, brs) 3.97(4H, q, J=7.2 Hz) 7.64(1H, ddd, J=8.6, 7.2, 1.0 Hz) 7.90(1H, ddd, J=8.4, 7.2, 1.0 Hz) 7.98(1H, dd, J=8.6, 1.0 Hz) 8.49(1H, dd, J=8.4, 1.0 Hz) 8.59(1H, s)

Example 45

4-Diethylamino-8-methoxyquinazoline hydrochloride

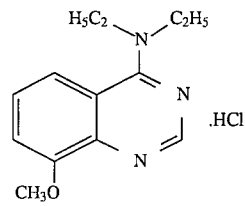

Mol. form. C₁₃H₁₇N₃O.HCl
Yield 96%
M.p. 198° to 199° C.
NMR δ (CDCl₃); 1.51(6H, brs) 3.96(4H, q, J=7.2 Hz) 4.13(3H, s) 7.29(1H, dd, J=7.6, 1.4 Hz) 7.51(1H, dd, J=8.8, 1.4 Hz) 7.55(1H, dd, J=8.8, 7.6 Hz) 8.93(1H, s)

Example 46

7-Chloro-4-diethylaminoquinazoline hydrochloride

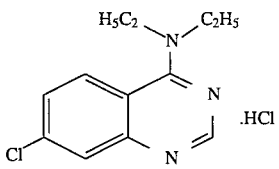

Mol. form. C₁₂H₁₄ClN₃.HCl
Yield 61%
M.p. 245° to 247° C.
NMR δ (CDCl₃); 1.53(6H, brs) 3.95(4H, q, J=7.2 Hz) 7.57(1H, dd, J=9.2, 2.0 Hz) 7.89(1H, d, J=9.2 Hz) 8.51(1H, d, J=2.0 Hz) 8.57(1H, s)

Example 47

6-Chloro-4-diethylaminoquinazoline hydrochloride

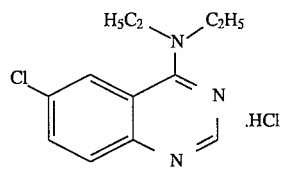

Mol. form. C₁₂H₁₄ClN₃.HCl
Yield 66%
M.p. 219° to 220° C.
NMR δ (CDCl₃); 1.64(6H, brs) 3.96(4H, q, J=7.2 Hz) 7.85(1H, dd, J=8.8, 2.0 Hz) 7.93(1H, d, J=2.0 Hz) 8.54(1H, d, J=8.8 Hz) 8.58(1H, s)

Example 48

6-Chloro-4-cyclopentylaminoquinazoline hydrochloride

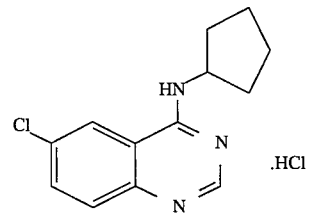

Mol. form. $C_{13}H_{14}ClN_3 \cdot HCl$
Yield 87%
M.p. 239° to 241° C.
NMR δ (CDCl$_3$); 1.65–1.74(2H, m) 1.88–2.00(2H, m) 2.00–2.12(2H, m) 2.12–2.22(2H, m) 4.86(1H, sextet, J=7.4 Hz) 7.61(1H, dd, J=8.8, 2.0 Hz) 8.12(1H, d, J=8.8 Hz) 8.55(1H, s) 9.20(1H, d, J=2.0 Hz) 9.86(1H, brd, J=7.4 Hz)

Example 49

4-Diethylamino-5,6-dimethoxyquinazoline

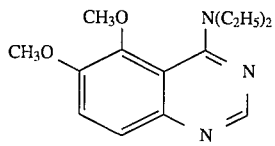

Mol. form. $C_{14}H_{19}N_3O_2$
Yield 70%
M.p. oily substance
NMR δ (CDCl$_3$); 1.23(6H, t, J=7.0 Hz) 3.61(4H, q, J=7.0 Hz) 3.72(3H, s) 3.98(3H, s) 7.49(1H, d, J=9.0 Hz) 7.63(1H, d, J=9.01 Hz) 8.47(1H, s)

Example 50

4-Diethylamino-2-methyl-6,7,8-trimethoxyquinazoline hydrochloride

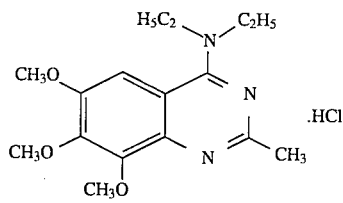

Mol. form. $C_{16}H_{23}N_3O_3 \cdot HCl$
Yield 85%
M.p. 186° to 187° C.
NMR δ (CDCl$_3$); 1.49(6H, q, J=7.0 Hz) 3.05(3H, s) 3.90(4H, J=7.0 Hz) 3.96(3H, s) 4.08(3H, s) 6.98(1H,

Example 51

2-Chloro-4-diethylamino-6,7,8-trimethoxyquinazoline

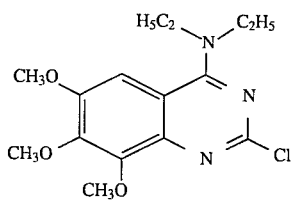

Mol. form. $C_{15}H_{20}ClN_3O_3$
Yield 75%
M.p. 107° to 108° C.
NMR δ (CDCl$_3$); 1.40(6H, q, J=7.2 Hz) 3.70(4H, q, J=7.2 Hz) 3.93(3H, s) 4.05(3H, s) 4.08(3H, s) 6.98(1H, s)

Example 52

4-Diethylamino-2-(4-hydroxypiperidino)-6,7,8-trimethoxyquinazoline hydrochloride

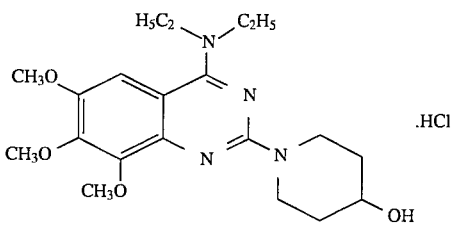

Mol. form. $C_{20}H_{30}N_4O_4 \cdot HCl$
Yield 53%
M.p. 77° to 78° C.
NMR δ (CD$_3$OD); 1.48(6H, t, J=7.2 Hz) 1.63(2H, m) 2.00(2H, m) 3.59(2H, m) 3.89(4H, q, J=7.2 Hz) 3.95(3H, s) 3.97(1H, m) 4.02(3H, s) 4.06(3H, s) 4.16(2H, m) 7.15(1H, s)

Example 53

4-Diethylamino-2-(4-ethoxycarbonylpiperidino)-6,7,8-trimethoxyquinazoline

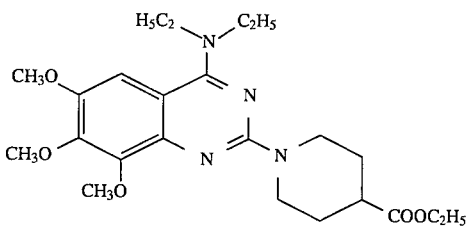

Mol. form. $C_{23}H_{34}N_4O_5$
Yield 36%
M.p. 80° to 81° C.
NMR δ (CDCl$_3$); 1.26(3H, t, J=7.2 Hz) 1.34(6H, t, J=7.2 Hz) 1.73(2H, m) 1.97(2H, m) 2.55(1H, m) 3.02(2H, m) 3.58(4H, q, J=7.2 Hz) 3.88(3H, s) 4.03(3H, s) 4.08(3H, s) 4.14(2H, q, J=7.2 Hz) 4.78(2H, m) 6.88(1H, s)

Example 54

2-(4-Carboxypiperidino)-4-diethylamino-6,7,8-trimethoxyquinazoline

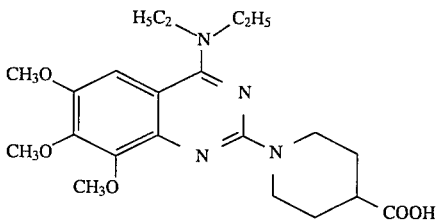

Mol. form. $C_{21}H_{30}N_4O_5$
Yield 38%
NMR δ (DMSO-d$_6$); 1.31(6H, t, J=7.0 Hz) 1.50(2H, m) 1.87(2H, m) 2.52(1H, m) 3.02(2H, m) 3.58(4H, brs) 3.83(3H, s) 3.85(3H, s) 3.95(3H, s) 4.57(2H, m) 6.89(1H, s) 12.23(1H, brs)

Example 55

6-Bromo-4-diethylamino-7,8-dimethoxyquinazoline hydrochloride

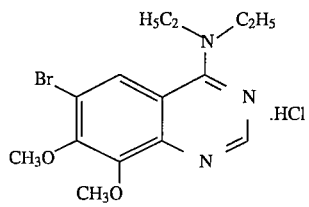

Mol. form. $C_{14}H_{18}BrN_3O_2 \cdot HCl$
Yield 75%
NMR δ (CDCl$_3$) 1.50(6H, brs) 3.93(4H, q, J=7.0 Hz) 4.13(3H, s) 4.19(3H, s) 7.94(1H, s) 8.84(1H, s)

Example 56

4-(4-Carbamoylpiperidino)-6,7,8-trimethoxyquinazoline

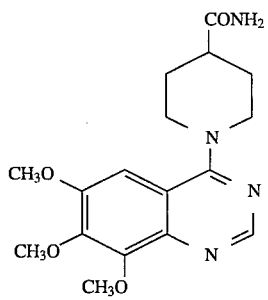

Mol. form. $C_{17}H_{22}N_4O_4$
Yield 81%
M.p. 165° to 166° C.
Mass 347 ($M^{30}$ +1)
NMR δ (CDCl$_3$) 2.00–2.10(4H, m) 2.50(1H, m) 3.09(2H, m) 3.97(3H, s) 4.06(3H, s) 4.13(3H, s) 4.20(2H, m) 5.56(1H, brs) 5.64(1H, brs) 6.93(1H, s) 8.73(1H, s)

Example 57

4-[4-(4-Fluorobenzoyl)piperidino]-6,7,8-trimethoxyquinazoline

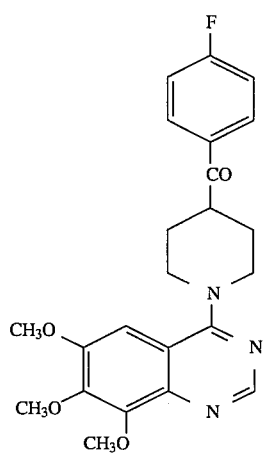

Mol. form. $C_{23}H_{24}FN_3O_4$
Yield 84%
M.p. 137° to 138° C.
Mass 426 ($M^+$+1)
NMR δ (CDCl$_3$) 2.03–2.15(4H, m) 3.21(2H, m) 3.56(1H, m) 3.97(3H, s) 4.07(3H, s) 4.14(3H, s) 4.23(2H, m) 6.95(1H, s) 7.19(2H, m) 8.04(2H, m) 8.75(1H, s)

Example 58

4-[4-(4-Fluoro-α-hydroxybenzyl)piperidino]-6,7,8-trimethoxyquinazoline

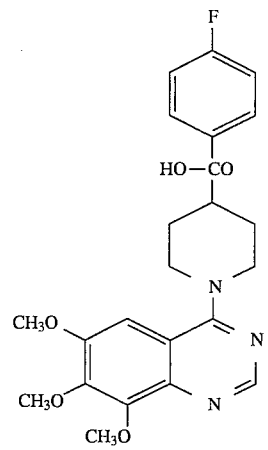

Mol. form. $C_{23}H_{26}FN_3O_4$
Yield 90%
M.p. 187° to 188° C.
Mass 428 ($M^+$+1)
NMR δ (CDCl$_3$) 1.42–1.53(2H, m) 1.57–1.68(2H, m) 1.92(1H, m) 2.16(1H, m) 2.92–3.07(2H, m) 3.95(3H, s) 4.05(3H, s) 4.12(3H, s) 4.10–4.30(2H, m) 4.49(1H, d, J=7.2 Hz) 6.90(1H, s) 7.07(2H, m) 7.33(2H, m) 8.70(1H, s)

Example 59

4-(4-Dimethylaminopiperidino)-6,7,8-trimethoxyquinazoline dihydrochloride

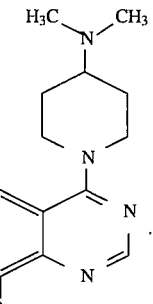

Mol. form. $C_{18}H_{26}N_4O_3 \cdot 2HCl$
Yield 55%
M.p. 197° to 198° C. (dec.)
Mass 347 ($M^+$+1)
NMR δ (CDCl$_3$) 1.90(2H, m) 2.29(2H, m) 2.73(6H, d, J=5.2 Hz) 3.55(2H, m) 3.66(1H, m) 4.010(3H, s) 4.012(3H, s) 4.03(3H, s) 4.84(2H, m) 7.24(1H, s) 8.70(1H, s) 11.35(1H, brs)

Example 60

4-(4-piperidinopiperidino)-6,7,8-trimethoxyquinazoline dihydrochloride

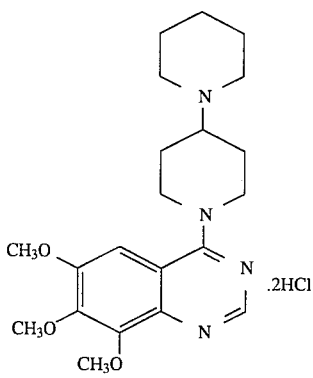

Mol. form. $C_{21}H_{30}N_4O_3 \cdot 2HCl$
Yield 92%
M.p. 219° to 220° C. (dec.)
Mass 347 (M$^+$+1)
NMR δ (CDCl$_3$) 1.55(1H, m) 1.82–2.08(7H, m) 2.40(2H, m) 3.05(2H, m) 3.53–3.75(5H, m) 4.06(3H, s) 4.10(3H, s) 4.13(3H, s) 5.05(2H, m) 7.24(1H, s) 8.58(1H, s)

Example 61

4-(4-Oxopiperidino)-6,7,8-trimethoxyquinazoline

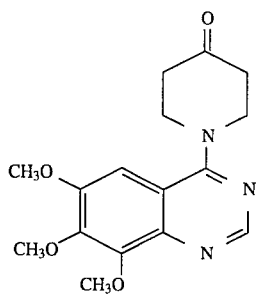

Mol. form. $C_{16}H_{19}N_3O_4$
Yield 66%
M.p. 135° to 136° C.
Mass 318 (M$^+$+1)
NMR δ (CDCl$_3$) 2.68(4H, t, J=6.0 Hz) 3.98(3H, s) 4.00(4H, J=6.0 Hz) 4.08(3H, s) 4.15(3H, s) 6.97(1H, 8.77(1H, s)

Example 62

4-(4-Hydroxypiperidino)-6,7,8-trimethoxyquinazoline

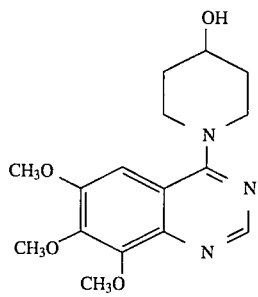

Mol. form. $C_{16}H_{21}N_3O_4$
Yield 83%
M.p. 150° to 151° C.
Mass 320 (M$^+$+1)
NMR δ (CDCl$_3$) 1.79(2H, m) 2.11(2H, m) 3.33(2H, m) 3.97(3H, s) 3.98–4.08(3H, m) 4.06(3H, s) 4.13(3H, s) 6.92(1H, s) 8.72(1H, s)

Example 63

4-Pyrrolidino-6,7,8-trimethoxyquinazoline hydrochloride

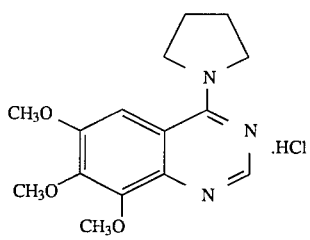

Mol. form. $C_{15}H_{19}N_3O_3 \cdot HCl$
Yield 11%
M.p. 156° to 157° C.
Mass 290 (M$^+$+1)
NMR δ (CDCl$_3$) 2.12(2H, brs) 2.23(2H, brs) 4.00(2H, brs) 4.03(3H, s) 4.09(3H, s) 4.16(3H, s) 4.29(2H, brs) 7.39(1H, s) 8.64(1H, s)

Example 64

4-Piperidino-6,7,8-trimethoxyquinazoline hydrochloride

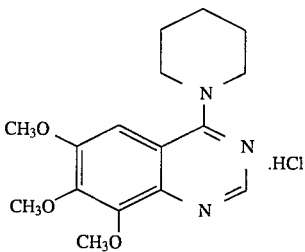

Mol. form. $C_{16}H_{21}N_3O_3 \cdot HCl$
Yield 85%
M.p. 145° to 146° C.
Mass 304 (M$^+$+1)
NMR δ (CDCl$_3$) 1.87(6H, brs) 3.98(3H, s) 4.09(3H, s) 4.11(4H, brt) 4.19(3H, s) 6.95(1H, s) 8.75(1H, s)

Example 65

4-[4-(2-Pyrimidyl)piperazin-1-yl]-6,7,8-trimethoxyquinazoline

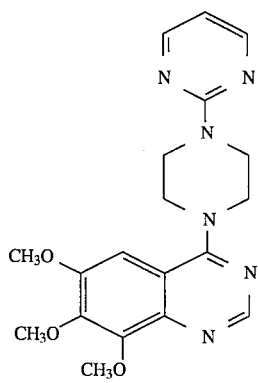

Mol. form. $C_{19}H_{22}N_6O_3$
Yield 86%
M.p. 157° to 158° C.
Mass 383 ($M^+$+1)
NMR δ (CDCl$_3$) 3.75(4H, m) 3.97(3H, s) 4.06(4H, m) 4.08(3H, s) 4.14(3H, s) 6.57(1H, t, J=4.8 Hz) 6.99(1H, s) 8.37(2H, d, J=4.8 Hz) 8.76(1H, s)

Example 66

4-[4-(2-Pyridyl)piperazin-1-yl]-6,7,8-trimethoxyquinazoline

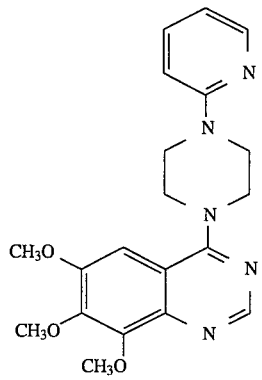

Mol. form. $C_{20}H_{23}N_5O_3$
Yield 80%
M.p. 145° to 146° C.
Mass 382 ($M^+$+1)
NMR δ (CDCl$_3$) 3.79(8H, brs) 3.97(3H, s) 4.08(3H, s) 4.14(3H, s) 6.69 (1H, ddd, J=7.2, 4.8, 0.8 Hz) 6.75(1H, dt, J=8.8, 0.8 Hz) 7.00(1H, s) 7.55(1H, ddd, J=8.8, 7.2, 2.0 Hz) 8.24(1H, ddd, J=4.8, 2.0, 0.8 Hz) 8.77(1H, s)

Example 67

4-(4-Dimethylaminopiperidino)-6,7,8-trimethoxyquinazoline

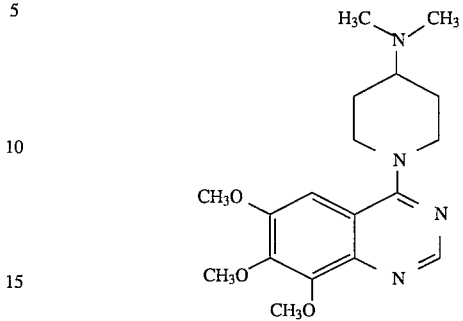

Mol. form. $C_{18}H_{26}N_4O_3$
Yield 42%
M.p. 182° to 184° C.
Mass 347 ($M^+$+1)
NMR δ (CDCl$_3$) 2.05(2H, m) 2.36(2H, m) 2.82(6H, s) 3.15(2H, m) 3.37(1H, m) 3.98(3H, s) 4.07(3H, s) 4.14(3H, s) 4.36(2H, m) 6.87(1H, s) 8.75(1H, s)

Example 68

4-Morpholino-6,7,8-trimethoxyquinazoline hydrochloride

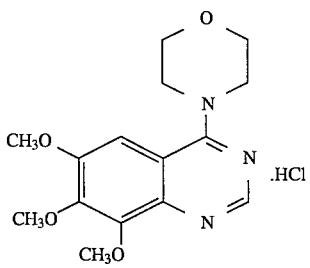

Mol. form. $C_{15}H_{19}N_3O_4 \cdot HCl$
Yield 84%
M.p. 158° to 159° C.
Mass 306 ($M^+$+1)
NMR δ (CDCl$_3$) 3.87(4H, t, J=4.4 Hz) 3.99(3H, s) 4.11(3H, s) 4.20(3H, s) 4.24(4H, t, J=4.4 Hz) 6.93(1H, s) 8.82(1H, s)

Example 69

4-(3-Carboxypropyl)amino-6-chloroquinazoline

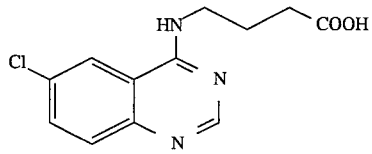

Mol. form. $C_{12}H_{12}ClN_3O_2$
Yield 78%
M.p. 257° to 258° C. (dec.)
NMR δ (DMSO-d$_6$); 1.85(2H, quintet, J=7.2 Hz) 2.31(2H, t, J=7.2 Hz) 3.52(2H, dt, J=7.2, 5.2 Hz) 7.67(1H, d, J=8.8 Hz) 7.75(1H, dd, J=8.8, 2.4 Hz) 8.34(1H, brt, J=5.2 Hz) 8.39(1H, d, J=2.4 Hz) 8.44(1H, s) 12.07(1H, brs)

Example 70

4-(3-Carboxypropyl)amino-7-chloroquinazoline

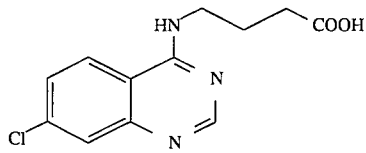

Mol. form. $C_{12}H_{12}N_3O_2$
Yield 89%
M.p. 243° to 244° C. (dec.)
NMR δ (DMSO-$d_6$); 1.87(2H, quintet, J=7.2 Hz) 2.33(2H, t, J=7.2 Hz) 3.55(2H, dt, J=7.2, 5.6 Hz) 7.67(1H, dd, J=8.8, 2.4 Hz) 7.71(1H, d, J=2.4 Hz) 8.28(1H, d, J=8.8 Hz) 8.44(1H, brt, J=5.6 Hz) 8.46(1H, s) 12.09(1H, brs)

Example 71

6-Chloro-4-diethylamino-7,8-dimethoxyquinazoline hydrochloride

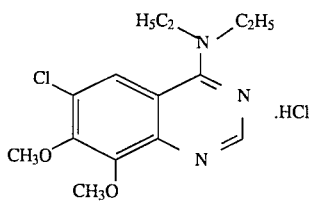

Mol. form. $C_{14}H_{18}ClN_3O_2$.HCl
Yield 83%
M.p. 129° to 130° C. (dec.)
NMR δ (CDCl$_3$); 1.87(2H, quintet, J=7.2 Hz) 2.33(2H, t, J=7.2 Hz) 3.55(2H, dt, J=7.2, 5.6 Hz) 7.67(1H, dd, J=8.8, 2.4 Hz) 7.71(1H, d, J=2.4 Hz) 8.28(1H, d, J=8.8 Hz) 8.44(1H, brt, J=5.6 Hz) 8.46(1H, s) 12.09(1H, brs)

Example 72

6-Bromo-4-diethylamino-7,8-dimethoxyquinazoline hydrochloride

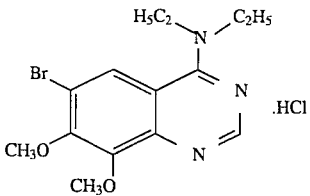

Mol. form. $C_{14}H_{18}BrN_3O_2$.HCl

Yield 75%
M.p. 148° to 149° C.
NMR δ (CDCl$_3$); 1.50(6H, brs) 3.93(4H, q, J=7.0 Hz) 4.13(3H, s) 4.19(3H, s) 7.94(1H, s) 8.84(1H, s)

Example 73

4-Diethylamino-7-methoxy-6-methylthioquinazoline hydrochloride

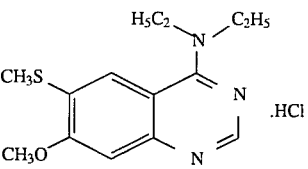

Mol. form. $C_{14}H_{19}N_3O_2$.HCl
Yield 67%
M.p. 213° to 214° C.
NMR δ (CDCl$_3$); 1.51(6H, t, J=7.0 Hz) 2.51(3H, s) 3.92(4H, q, J=7.0 Hz) 4.11(3H, s) 7.55(1H, s) 7.86(1H, s) 8.48(1H, s)

We claim:

1. A compound or a pharmacologically acceptable salt thereof selected from the group consisting of:

4-(3-ethoxycarbonylpropyl)amino-6,7,8-trimethoxy-quinazoline;

4-(3-carboxypropyl)amino-6,7,8-trimethoxy-quinazoline;

4-(5-ethoxycarbonylpentyl)amino-6,7,8-trimethoxy-quinazoline;

4-(5-ethoxycarbonylpentyl)amino-6-chloro-quinazoline;

4-(ethoxycarbonylmethyl)amino-6,7,8-trimethoxy-quinazoline; 4-(6-ethoxycarbonylhexyl)amino-6,7,8-trimethoxy-quinazoline; 4-(2-ethoxycarbonylethyl)amino-6,7,8-trimethoxy-quinazoline; 4-(4-ethoxycarbonylbutyl)amino-6,7,8-trimethoxy-quinazoline; 4-(7-ethoxycarbonylheptyl)amino-6,7,8-trimethoxy-quinazoline; 4-(5-carboxypentyl)amino-6-chloroquinazoline; and 4-(carboxymethyl)amino-6,7,8-trimethoxy-quinazoline.

2. A pharmaceutical composition comprising a compound of claim 1 and a pharmaceutically acceptable carrier or diluent.

3. A method of inhibiting phosphodiesterase comprising administering to a patient in need of same a compound of claim 1.

* * * * *